United States Patent [19]

Savion et al.

[11] Patent Number: 6,126,947
[45] Date of Patent: *Oct. 3, 2000

[54] METHOD FOR THE TREATMENT OF SKIN DISORDERS USING INHIBITOR OF CHOLESTEROL SYNTHESIS

[75] Inventors: Naphtali Savion, Givat Shmuel; Sara Brenner, Herzlia-Pituach, both of Israel

[73] Assignee: Ramot Univ. Authority for App. Research & Indus. Dev. Ltd., Ramat-Aviv, Israel

[ * ] Notice: This patent is subject to a terminal disclaimer.

[21] Appl. No.: 08/950,764

[22] Filed: Oct. 15, 1997

Related U.S. Application Data

[63] Continuation-in-part of application No. 08/615,266, filed as application No. PCT/US95/11678, Sep. 13, 1995, Pat. No. 5,730,992.

[30] Foreign Application Priority Data

Sep. 13, 1994 [IL] Israel .......................................... 110943

[51] Int. Cl.$^7$ ...................................................... A61K 7/48
[52] U.S. Cl. ........................... 424/401; 514/460; 514/864; 514/880; 514/859; 514/944; 514/969
[58] Field of Search ............................ 424/401; 514/460, 514/859, 944, 969, 864, 880

[56] References Cited

U.S. PATENT DOCUMENTS 4,231,938 11/1980 Monaghan et al. .
5,730,992 3/1998 Sanion et al. ............................ 424/401

OTHER PUBLICATIONS

*J.S. Strauss, "Pathogenesis of Acne: How Might Azelaic Acid Act?", Journal of Dermatological Treatment (1989) I, 3–6.

*H. Gollnick, "The New Therapeutic Agent: Azelaic Acid in Acne Treatment", Journal of Dermatological Treatment (1990) 1 (Suppl 3): S23–S28.

*Goldstein, Joseph L. and Brown, Michael S., "Regulation of the Mevalonate Pathway", Nature, vol. 343, Feb. 1, 1990, 425–430.

*The Merck Index, An Encyclopedia of Chemicals, Drugs and Biologicals, 11th Edition, 1989.

Negre–Aminou, Pascale et al., Biochimica et Biophysica Acta 1345 (1997) 259–268.

Amin, Dilip et al., The Journal of Pharmacology and Experimental Therapeutics, vol. 281, No. 2, 1997, 746–752.

Eisele, Bernhard et al., Journal of Lipid Research, vol. 38, 1997, 564–575.

*Primary Examiner*—Jyothsan Venkat
*Attorney, Agent, or Firm*—Blank Rome Comisky & McCauley LLP

[57] ABSTRACT

An inhibitor of cholesterol synthesis is used for the treatment, alleviation or prevention of skin disorders.

12 Claims, No Drawings

METHOD FOR THE TREATMENT OF SKIN DISORDERS USING INHIBITOR OF CHOLESTEROL SYNTHESIS

This application is a continuation-in-part of application Ser. No. 08/615,266, filed on Mar. 13, 1996 now U.S. Pat. No. 5,730,992, which is a National Phase Application of International Application No. PCT/US95/11678 filed Sep. 13, 1995.

FIELD OF THE INVENTION

The present invention is generally in the field of compositions for topical application onto the skin intended to improve the skin's condition. The present invention provides a method useful for improving various skin conditions.

BACKGROUND OF THE INVENTION

Acne is a chronic inflammatory disorder of the pilosebaceous follicles, particularly in the face and neck region, occurring most commonly in adolescence between the ages of about 14 to about 19. Acne involves increased sebum secretion, hyperkeratinization in the infrainfundibulum of the follicular duct, increased microbial colonization and inflammation (Straiss, (J. S., *J. Dermatol. Treat.*, 1:3–6 (1989)). Various methods for the treatment of acne and other sebaceous glands' inflammation have been proposed, ranging from special diets, prevention of contact of the skin by known acneignic agents (e.g., low grade cosmetics), use of endocrine preparations containing progesterone or estrogen, and others, most of which have not proved to be effective. Additionally, it has also been proposed to use antiseptic, antibacterial and wide-spectrum antibiotic compounds in both topical and systemic application.

All hitherto used anti-acne agents were effective in suppressing the development of microbial population, keratinization and comedo formation in the sebaceous glands. However, only few of the anti-acne agents hitherto used were effective in the reduction of the sebum excretion rate (Gollnick, H., *J. Dermatol. Treat.* 1:S23–S28 (1990) and none of the agents was useful in affecting lipid biosynthesis in the pilosebaceous unit.

Xerosis in the "dry" rough quality of skin, particularly old skin, which origin is quite convertical, although this surface irregularity may also be attributed simply to slower transit of corneocytes through the stratum corncum allowing accumulation of damage in situ.

The term "Ichtyosiform dermatoses", also at times termed hereinafter as "Ichthyosis", concerns a heterogenous group of heriditary disorders, allow which are characterized by the accumulation of large amounts of scale on the cutaneous surface.

Rosacea was originally termed "acne rosacea" which is an inappropriate term that still persists. Papules and papulo-pustules occur in the central region of the face against a vivid erythematous background with telangiectases. Later, there may occur diffuse hyperplasia of connective tissue with enlarged sebaceous glands. The disease evolves in stages. The early signs are recurrent episodes of blushing that finally become persistent dark red erythema, particularly on the nose and cheeks, often before the age of twenty. These persons are the so-called flushers and blushers. Rosacea is common in the third and fourth decades and peaks between the ages of 40 to 50 years. In the worst cases, disfiguring hypertrophy, particularly of the nose which is termed "rhinophyma" may develop after many years.

Allergic contact dermatitis is usually evident by acute erruptions which are characterized by macular erytherma and papules, vesicles or bullae, which occur after contact with the allergens. At its initiation, contact dermitis usually involves the cutaneous site of principal exposure, i.e. the region which comes into direct contact with the allergen. However, if it evolves, it can spread to other more distant sites, either by inadvertent contact or under certain circumstances by auto-sensitization.

Atopic dermatitis also termed "atopic eczema" is a chronically relapsing skin disorder that arises most commonly during infancy childhood or adolescence. The main syndrome in atopic dermatitis is the characteristic "itch" which causes scratching, prurigo papules, lichenification and eczematous lesions.

Seborrheic dermatitis is common and usually easily recognized. It affects babies and adults and is often associated with increased sebum production (seborrhea) of the scalp and the sebaceous folicle-rich areas of the face and trunk. The affected skin is pink, edematous, and covered with yellow-brown scales and crusts. The disease has a wide range from mild to severe including psoriasi-form patterns and erythroderma.

Isoprenoid groups such as cholesterol, squalene and cholesterylesters are synthesized via the mevalonate pathway (Goldstein, J. L., Brown, M. S., *Nature*, 34B, 425 (1990)), wherein the end-product is cholesterol. One of the key enzymes which regulate the production of mevalonate, the precursor of the above isoprenoid groups, is the 3-hydroxy-3-methyl-glutaryl coenzyme A (HMG-CoA) reductase. Inhibitors of this enzyme inhibit the synthesis of cholesterol and are thus used as antihypercholesterolemic medicaments for the treatment of arteriosclerosis, hyperlipemia and related diseases. Example of such an inhibitor is Lovastatin (Merck Index 5460, U.S. Pat. No. 4,231,938), Fluvastatin (XU 62-320, EP 0114 027), Paravastatin (Merck Index 7712, U.S. Pat. No. 4346,227), Simvastatin (Merck Index 8491, U.S. Pat. No. 4,444,784); Atorvastatin (CI-981), Cerivastatin (BAY W6228) and Crilvastatin (Pan Medica, Carros France) (all mentioned in Nègre-Aminou et al., *Biochimica et Biophysica Acta* 1345:259–268 (1997)). Pharmaceutical compositions comprising this inhibitor of HMC-CoA reductase are given orally or parenterally to patients suffering from arteriosclerosis or hyperlipemia.

SUMMARY OF THE INVENTION

In accordance with the invention it has surprisingly been found that several skin disorders such as: acne, seborrhea, rosacea, atopic dermatitis, contact dermatitis, ichthyosis and rhinophyma can be treated by one topical application of one of a plurality of cholesterol synthesis inhibitors. In accordance with the invention there is thus provided a method for treatment of skin disorders by topical application of an inhibitor of cholesterol synthesis.

In accordance with the present invention there is thus provided a composition for topical skin application comprising a carrier and, as an active ingredient, an effective amount of an inhibitor of cholesterol synthesis.

The topical composition of the invention may be a pharmaceutical or cosmetic composition. While inhibitors of cholesterol synthesis were previously administered orally or parenterally for lowering the cholesterol level of the patient they were never formulated as a topical composition so that the topical composition per se is novel.

The topical composition of the invention may be used for various indications including acne, scalp dandruff, seborrhea, rosacea, rhinophyma, atopic dermatitis, contact dermatitis, ichthyosis, xerosis (dry skin) aging (including wrinkles and pigmentation), sun damage including solar keratosis.

Also provided by the invention is a method for improvement of skin condition comprising topically applying onto the skin a composition comprising a carrier and, as an active ingredient, an effective amount of an inhibitor of cholesterol synthesis. A particular application of the method is the treatment, alleviation or prevention of acne, scalp dandruff, seborrhea, rosacea, rhinophyma, atopic dermatitis, contact dermatitis, ichthyosis, xerosis, aging and solar-caused skin damage. The method can cause improvement of the skin condition or alleviation of some symptoms as can be determined by clinical acceptable criteria, or the method can be used as a preventive measure in order to prevent occurrence of the skin disorder in the first place, for example by chronic administration.

The term "effective amount" should be understood as meaning an amount of an active ingredient needed to achieve a desired therapeutic or cosmetic effect. For example, in a pharmaceutical composition of the invention an effective amount of an inhibitor of cholesterol synthesis is an amount which is sufficient, in the administration regimen of the pharmaceutical composition in the framework of treatment, to achieve an improvement in the skin's condition. In a cosmetic composition, an effective amount is an amount which causes an improvement in skin appearance.

Inhibitors of cholesterol synthesis useful in accordance with the present invention are various agents which inhibit the production of the end product, i.e. cholesterol, or any of the intermediates of the various steps of the mevalonate pathway in which cholesterol is produced from the precursors acety CoA and acetoacetyl CoA. The inhibitors can be agents which inhibit the enzymes involved in the various steps of these biosynthetic pathways and sequalene biosynthesis [BIBB 515 -(1-(4-chlorobenzoyl)-4-4-((4-(2-oxazolin-2-yl-)-benzylidene)) piperidine]; an inhibitor of 2,3-oxidosqualene cyclase (OSC) or PRP107393 an inhibitor of sequalene synthase. Alternatively the invention may be an inhibitor of the enzyme Acyl-CoA; cholesterol acyl transferase which is responsible for cholesterol esterification for example di- and tri- fluorophenyl, n-heptyl and benzyl substituents (Bernhard Eisele et al., *Journal of Lipid Research,* 38:564–575 (1997); Amin et al, *The Journal of Pharmacology and Experimental Therapeutics,* 281(2):746–752 (1997); Purchase et al., *Biorganic & Medicinal Chemistry,* 5(4):739–747, (1997)). The inhibitors of cholesterol synthesis may also be agents which serve as sequesters of the intermediates in the cholesteral pathway, both of which reduce the amount of cholesterol produced in this process.

In accordance with a preferred embodiment of the invention, the inhibitor of cholesterol synthesis is an agent which inhibits the HMG-CoA reductase, such as Lovastatin, Fluvastatin, Pravastatin Simvastatin, Atervastatin, Cerivastatin and Crilvastatin.

The concentration of the active ingredient is 0.05–50% preferably about 0.2–10% and most preferably about 2%.

The topical composition of the invention when used for the treatment of acne may further comprise various other anti-acne agents, agents such as: antimicrobial (e.g. antibiotics) agents, for the treatment or prevention of a secondary infection, skin peeling agents, retinoides such as retin A, separately or together with resorcinol.

Where the topical composition of the invention is used for the treatment of seborrhea, the topical composition may be in the form of a shampoo, a soap, a detergent etc. and may comprise other anti-seborrhea agents such as selenium sulfide, anti-fungal anti-bacterial and anti-trychomonas agents, zinc peridione, salicylic acid and benzoyl peroxide.

Where the topical composition of the invention is intended for the treatment of contact dermatitis or atopic dermatitis, it may comprise also steroids, glucocorticoids, in aqueous or lipid carriers such as lanoline or vaseline and may be in the form of salve, cream or ointment. For the treatment of atopic dermatitis, the composition can further comprise hydrating agents such as lactic acid.

Where the topical composition of the invention is intended for the treatment of ichthyosis it can comprise hydrating agents such as lactic acid, urea and emulants.

Where the topical composition is intended to be used for the treatment of xerosis (dry skin), resulting from genetic, environmental (sun, detergents) or age-related causes, the composition can comprise also hydrating agents and emulsifying agents.

It should be emphasized that the topical composition may be pharmaceutical or cosmetic, the latter for example for the improvement of aging skin i.e. improvement of age-related wrinkles and pigmentation. Where the composition of the invention is an anti-aging cosmetic composition, it may further contain other known anti-aging agents such as fruit acids, retin A, peeling agents, anti-oxidents, hydrating agents etc.

The topical composition may also be used for preventing or minimizing sun-damage, for example, in sun tanning preparation, or may be present in tanning preparations and in such cases may include also sun-blocking agents (for tanning preparations) and anti-aging agents (for after tanning preparations).

Where the topical composition is intended for the treatment of Rosacea rhinophyma, it can also include anti-trichomonatic agents such as metronidazol as well as steroids.

The carriers of the topical composition of the present invention may be any pharmaceutically or cosmetically acceptable carriers such as, for example, ethanol, gel, liposome formulation, ointment, salve, cream, etc. The carrier should be chosen in accordance with the properties (lipophilic, hydrophilic) of each specific active ingredient. For cosmetic purposes the carrier may be a face cream, a shampoo, a soap, a detergent, a sun tanning preparation, etc.

EXAMPLES

Example I
Preparation of compositions for topical skin applications:
Four commonly available inhibitors of cholesterol synthesis were used: Fluvastatin™, Pravastatin™, Lovastatin™ and Simvastatin™.

a. Preparation of Fluvastatin solution:
30 capsules of 20 mg each were opened and the gritty powder was dissolved in 15 ml of purified pyrogen-free water (Travenol), filtered through ordinary laboratory paper, followed by a wash with 15 ml of water, giving a final volume of 30 ml which makes 2% solution.

b. Preparation of Fluvastatin Shampoo:
The 2% Fluvastatin solution (5 ml) prepared as above was mixed with standard shampoo for normal hair (10 ml) giving a final putative concentration of 0.66%.

c. Preparation of Pravastatin solution:
30 tablets of 20 mg each were ground by mortar and pestle; 15 ml of water as described above were added. The solution was filtered and washed as above, to give a final putative concentration of 2%.

d. Preparation of Lovastatin solution:

Was carried out as described above for Pravastatin but using 70% alcohol solution instead of water.

c. Preparation of Simvastatin solution:

Was carried out as described above for Lovastatin.

Example II

Method of Treatment:

Patients with different skin disorders were treated by applying the prepared solution to the affected area with the "fingertips" twice daily. Patients were instructed not to wash the treated area for at least 6 hours following application. The effect of the treatment was evaluated 3 days, and one, two, four and six weeks after initiation of the treatment and every six weeks thereafter (whenever treatment was continued).

Example III

Treatment of acne by Lovastatin

A. Trial 1

Pharmaceutical compositions containing Lovastatin prepared as described above were topically applied twice daily for a period of 12 weeks, to the faces of two individuals suffering from acne vulgaris. The patients were required to discontinue all other topical and systemic anti-acne treatment 30 days prior to the beginning of the trial and discontinued all facial and cosmetic treatment seven days prior to the onset of treatment.

The acne condition was assessed by recording all acne lesions including inflamed acne lesions (papules and pustules) and non-inflamed acne lesions, (white and black comedos) prior to the beginning of treatment and 4, 8 and 12 weeks following the onset of treatment.

In both patients, improvement in all mentioned lesions was noticed and at the end of the 12 week treatment period the number of lesions decreased to less than half. No side effects were noticed save for a mild dryness of the skin, which is likely a result of the ethanol.

B. Trial 2

4 patients, 16–25 years of age, consisting of 2 males and 2 females, having mild to moderate acne were treated with the above preparation. All medications and cosmetics were stopped for 14 days, following which the patients were asked to apply the preparation twice daily for 8 weeks and to refrain from using all other forms of treatment and cosmetics during treatment. Prior to and after 4 and 8 weeks of treatment, the number of acne lesions (papules, pustules and white and black comedos) was recorded, and the results, shown in the following Table 1 demonstrated an improvement in all 4 patients evidenced by reduction of the number of all types of lesions:

TABLE 1

Number of acne lesions before and during treatment

| Patient | Lesions | Before Treatment | After 1 month | After 2 months |
| --- | --- | --- | --- | --- |
| 1 | Pustules | 10 | 7 | 3 |
|  | Papules | 11 | 3 | 2 |
|  | White & blackheads | 18 | 10 | 7 |
| 2 | Pustules | 17 | 15 | 2 |
|  | Papules | 17 | 15 | 10 |
|  | White & blackheads | 18 | 15 | 6 |
| 3 | Pustules | 7 | 2 | — |
|  | Papules | 12 | 7 | 4 |
|  | White & blackheads | 22 | 14 | 7 |

TABLE 1-continued

Number of acne lesions before and during treatment

| Patient | Lesions | Before Treatment | After 1 month | After 2 months |
| --- | --- | --- | --- | --- |
| 4 | Pustules | 20 | 18 | 5 |
|  | Papules | 16 | 9 | 5 |
|  | White & blackheads | 15 | 10 | 5 |
| Average | Pustules | 13 | 10 | 2 |
|  | Papules | 14 | 8 | 5 |
|  | White & blackheads | 18 | 12 | 6 |

Example IV

Treatment of acne by other cholesterol inhibitors

With Fluvastatin solution—2 patients were treated with Fluvastatin for 2 weeks.

With Pravastatin—6 patients were treated with Pravastatin for 2 weeks;

With Simvastatin—2 patients were treated with Simvastatin for 2 weeks.

Clinical Results—All treated patients demonstrated significant reduction of 30 to 40% in all skin type lesions associated with acne such as comedos, papules and pustules determined as described above. No side effects were noted.

Example V

Treatment of Seborrhea:

a. With Pravastatin:

5 patients were treated for 3 to 7 days with Pravastatin as described above in connection with Lovastatin.

Clinical results—Complete disappearance of the lesions and the rash of the face (the treated area).

These patients were followed for 6 to 12 months with exacerbations of the seborrhea and were retreated for 3 to 5 days each time with complete disappearance after each treatment.

3 additional patients were treated for 1 week as described above demonstrated clinical improvement and discontinued so that no follow up was available.

b. With Fluvastatin solution:

12 patients were treated for 3 to 7 days with Fluvastatin as described above.

Clinical results—In 9 patients, complete disappearance of the seborrhea at the treated area was observed with no side effects; the condition of one patient was not improved, and the patient stopped the treatment after 1 week; 1 patient felt burning immediately upon application of the treatment and therefore stopped the treatment; 1 patient felt burning immediately upon application of the treatment but continued the treatment, eventually the burning sensation disappeared and the clinical condition was significantly improved. 1 patient was treated for 1 week with clinical improvement but discontinued the trial so that no further follow up was available.

c. With Fluvastatin shampoo:

6 patients with seborrheic dermatitis were treated by shampooing their scalp once with the Fluvastatin shampoo followed by immediate second shampooing.

Clinical results—4 patients showed alleviation of the dandruff and seborrheic dermatitis; 1 patient was not improved, and 1 patient discontinued the trial so that no follow up was available.

Example VI
Treatment of Rosacea and Rhinophyma:

With Fluvastatin:

4 patients were treated for 3 to 6 months as described above. 1 of the patients suffered also from Rhinophyma and treatment included his nose as well.

Clinical results —All patients demonstrated significant improvement showing less redness, less pronounced telangiectasias.

Example VII
Treatment of patients with Atopic Dermatitis and Contact Dermatitis (Eczema)

With Pravastatin:

2 patients demonstrating allergic contact to nickel on top of history of long standing atopic dermatitis applied a solution of Pravastatin twice daily.

Clinical results—After 3 days of treatment an improvement was noticed with no side effects.

Example VIII
Treatment of Ichthyosis:

a. With Fluvastatin:

3 patients with Ichthyosis were treated on a small area of 5×5 cm of affected body area twice daily for 1 week Clinical results—An improvement was noticed in all 3 of them: 1 patient suffered from burning sensation upon application of the solution but continued despite the burning which disappeared later on and showed clinical improvement.

b. With Pravastatin:

2 patients were treated as described above for Fluvastatin.

Clinical Results—Both patients demonstrated clinical improvement after one week of treatment, with no side effects.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for treating skin disorders comprising the step of topically applying to the skin a therapeutically effective amount of an inhibitor of the 3-hydroxy-3-methylglutaryl coenzyme A (HMG-CoA) reductase, wherein the skin disorder is selected from the group consisting of acne, scalp dandruff seborrhea, rosacea, rhinophyma, ichthyosis, atopic dermatitis, contact dermatitis, xerosis, age-caused wrinkles and pigmentation and sun damage.

2. The method according to claim 1, wherein the inhibitor is selected from the group consisting of: Lovastatin, Fluvastatin, Pravastatin, Simvastatin, Atorvastatin, Cerviv-astatin and Crivastatin.

3. The method according to claim 2, wherein the concentration of the inhibitor is about 0.05–50%.

4. The method according to claim 3, wherein the concentration of the inhibitor is 0.2–10%.

5. The method according to claim 4, wherein the concentration of the inhibitor is about 2%.

6. The method of claim 1 for the treatment of acne further comprising anti-acne agents selected from the group consisting of: antimicrobial agents, peeling agents and retinoids.

7. A method for the treatment of skin disorders comprising the step of topically applying to the skin a therapeutically effective amount of an inhibitor of cholesterol synthesis by way of the mevalonate pathway; said disorders selected from the group consisting of acne, dandruff, seborrhea, rosacea, dermatitus, ichthyosis, rhinophyma, xerosis, age-caused wrinkles and pigmentation and sun damage.

8. A method according to claim 7, wherein the inhibitor of cholesterol synthesis is an inhibitor of 3-hydroxy-3-methylglutaryl coenzyme A reductase (HMG-CoA reductase).

9. A method according to claim 8, wherein the inhibitor is selected from the group consisting of: Lovastatin, Fluvastatin, Pravastatin, Simvastatin, Atorvastatin, Cerviv-astatin and Crivastatin.

10. A method according to claim 9, wherein the concentration of the inhibitor is about 0.05–50%.

11. A method according to claim 10, wherein the concentration of the inhibitor is 0.2–10%.

12. A method according to claim 11, wherein the concentration of the inhibitor is about 2%.

\* \* \* \* \*

UNITED STATES PATENT AND TRADEMARK OFFICE
CERTIFICATE OF CORRECTION

PATENT NO. : 6,126,947
DATED : October 3, 2000
INVENTOR(S) : Naphtali Savion et al.

It is certified that error appears in the above-identified patent and that said Letters Patent is hereby corrected as shown below:

Title page,
Column 2,
Line 1, change "Sanion" to -- Savion --.

Column 1,
Line 23, change "Straiss" to -- Strauss --;
Line 49, change "allow" to -- all of --;

Column 3,
Line 31, change "acety" to -- acetyl --;
Line 34, change "-4-4-((," to -- 4-(( --;
Line 35, change "-2-yl-)" to -- 2-yl) --;
Line 38, after -CoA change the ";" to -- : --;
Line 54, change "Atervastatin" to -- Atorvastatin --;
Line 67, change "anti-seborrhea" to -- anti-seborrhic and anti-dandruff --.

Column 4,
Line 1, change "trychomonas" to -- trichomonas --.

Column 8, claim 2,
Line 3, change "Cerviv" to -- Ceriv --;
Line 4, change "Crivastatin" to -- Crilvastatin --;

Claim 9,
Line 3, change "Cerviv" to -- Ceriv --;
Line 4, change "Crivastatin" to -- Crilvastatin --.

Signed and Sealed this

Ninth Day of October, 2001

*Attest:*

NICHOLAS P. GODICI
*Attesting Officer*     *Acting Director of the United States Patent and Trademark Office*